United States Patent [19]

Khanna et al.

[11] Patent Number: 5,652,363

[45] Date of Patent: Jul. 29, 1997

[54] PYRIDO-1,4-OXAZINYLALKYL-BENZAMIDE DERIVATIVES

[75] Inventors: Ish Kumar Khanna, Vernon Hills; Michael Allan Stealey, Libertyville; Richard Mathias Weier, Lake Bluff, all of Ill.

[73] Assignee: C.D. Searle & Co., Skokie, Ill.

[21] Appl. No.: 725,285

[22] Filed: Oct. 2, 1996

Related U.S. Application Data

[60] Provisional application No. 60/005,052, Oct. 5, 1995.

[51] Int. Cl.6 .................................................. C07D 265/36
[52] U.S. Cl. ............................................................ 544/105
[58] Field of Search ............................ 544/105; 514/230.5

[56] References Cited

U.S. PATENT DOCUMENTS

| | | | |
|---|---|---|---|
| 3,854,926 | 12/1974 | Senkbeil | 71/94 |
| 4,243,671 | 1/1981 | Harris et al. | 424/273 |
| 4,284,641 | 8/1981 | Thorogood | 424/273 |
| 4,416,895 | 11/1983 | Thorogood | 424/273 |
| 4,451,650 | 5/1984 | Temple, Jr. et al. | 544/105 |
| 4,579,862 | 4/1986 | Manley et al. | 514/399 |
| 4,804,656 | 2/1989 | Andersson et al. | 514/179 |
| 4,914,108 | 4/1990 | Khanna et al. | 514/303 |
| 5,360,907 | 11/1994 | Lentz et al. | 546/113 |

FOREIGN PATENT DOCUMENTS 286173  1/1991  Germany.

*Primary Examiner*—Mukund J. Shah
*Assistant Examiner*—Tamthom T. Ngo
*Attorney, Agent, or Firm*—Fitzpatrick, Cella, Harper & Scinto

[57] ABSTRACT

The present invention relates to compounds of the formula

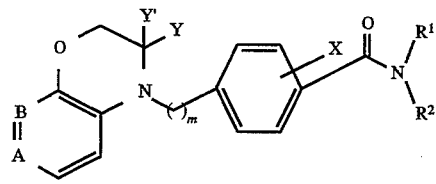

and pharmaceutical compositions containing a therapeutically effective amount of the compounds in combination with a pharmaceutically acceptable carrier and a method for treating diseases mediated by platelet activating factor.

35 Claims, No Drawings

PYRIDO-1,4-OXAZINYLALKYL-BENZAMIDE DERIVATIVES

This application claims the benefit of U.S. provisional application No. 60/005,052 filed Oct. 5, 1995.

FIELD OF THE INVENTION

This invention relates to compounds having platelet activating factor (PAF) antagonist activity which are useful for treating PAF mediated disorders such as asthma, cardiovascular diseases, cerebrovascular diseases, septic shock and the like. The present invention more particularly relates to a class of novel N,N-cycloalkyl/alkyl pyrido 1,4-oxazinylalkyl-benzamide derivatives which are PAF antagonists.

BACKGROUND OF THE INVENTION

Platelet-activating factor (PAF) has been associated with various biological activities and pathways, thus making it an important mediator responsible for variety of physiological processes, including activation of platelets, smooth muscle contraction, pathogenesis of immune complex deposition, inflammation, and respiratory, cardiovascular and intravascular alterations. These physiological processes are associated with a large group of diseases, such as cardiovascular disorders, asthma, lung edema, septic shock, adult respiratory distress syndrome and inflammatory diseases.

Various classes of compounds are known for inhibiting platelet activation induced by agents such as arachidonic acid, collagen and platelet activating factor. For example, U.S. Pat. No. 4,804,658 discloses a class of imidazopyridine derivatives useful in the treatment of diseases or disorders mediated by platelet-Iizuki, et al. mentions certain classes of imidazoles, which are described as having an inhibitory effect on thromboxane synthetase and as useful for treatment of inflammation, thrombus and asthma. U.S. Pat. Nos. 4,284,641 and 4,416,895 to Thorogood describe certain cycloalkyl/cycloalkenyl imidazoles which inhibit platelet aggregation or reduce the adhesive character of platelets by selective inhibition of thromboxane A2. U.S. Pat. No. 4,537,340 to Thorogood describes a class of 1-arylalkylimidazoles useful for the same purpose. In U.S. Pat. No. 4,243,671 to Harris, et al., the compound 1-(3-phenyl-2-propenyl)1H-imidazole is described as effective in inhibiting thromboxane synthetase, arachidonic acid-induced platelet aggregation and bronchoconstriction.

Compounds are known for use in treating platelet dysfunction or platelet hyperactivity induced specifically by platelet activating factor (PAF). For example, a certain class of glycerol derivatives useful as PAF antagonists is described in EP No. 142,333. A class of indene derivatives is described in EP No. 142,801 as PAF inhibitors. Compounds containing heterocyclic moieties of various types are also known as PAF antagonists. For example, U.S. Pat. No. 4,579,862 to Manley, et al. describes certain imidazole/pyridinylalkanoic acid derivatives as PAF antagonists. U.S. Pat. No. 4,914,108 to Khanna, et al. describes a class of 5-substituted imidazo[4,5-c]pyridine compounds having PAF antagonist activity. U.S. Pat. No. 5,360,907 to Lentz et al. discloses pyrrolo[3,2B]pyridinylalkylbenzamide derivatives which possess PAF antagonist activity.

SUMMARY OF THE INVENTION

This invention relates to a novel class of compounds represented by the formula I

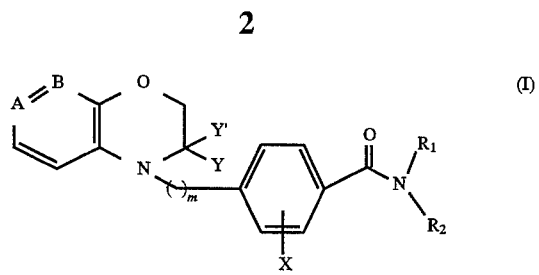

or a pharmaceutically acceptable salt thereof, wherein A-B is selected from the group of —N=CH— and —CH=N—;

m is an integer from 1 to 4;

$R_1$ and $R_2$ are each independently selected from the group consisting of hydrogen; straight or branched alkyl of 1 to 12 carbon atoms, cycloalkyl having 3 to 8 carbon atoms optionally substituted by one or more alkyl of 1 to 6 carbon atoms, bicycloalkyl having 3 to 8 carbon atoms in each ring, phenyl optionally substituted by one or more groups independently selected from the group consisting of alkyl having 1 to 6 carbon atoms and halogen, straight or branched alkenyl having 3 to 12 carbon atoms, and cycloalkenyl having 3 to 8 carbon atoms;

X is selected from the group consisting of hydrogen, halogen, cyano, hydroxy, amino, straight or branched alkyl of 1 to 6 carbon atoms, alkoxy, alkylthio, alkylamino, aminoalkyl, and hydroxyalkyl, wherein the alkyl moiety has 1 to 6 carbon atoms, alkoxyalkyl, alkylthioalkyl, alkylaminoalkyl, dialkylaminoalkyl, dialkylamino wherein each of the alkyl groups has 1 to 6 carbon atoms; and wherein Y and Y' are either both hydrogen or, taken together, are =O.

The present invention also provides pharmaceutical compositions comprised of a therapeutically effective amount of a compound of Formula I in combination with a pharmaceutically acceptable carrier and provides a method for treating diseases mediated by platelet-activating factor.

DETAILED DESCRIPTION OF THE INVENTION

This invention encompasses compounds of the Formula I as previously described.

Within the class of compounds defined by Formula I, there is a subclass of preferred compounds represented by the Formula I wherein $R_1$ and $R_2$ are independently selected from the group consisting of straight or branched chain alkyl of 1 to 6 carbon atoms and cycloalkyl of 3 to 7 carbon atoms.

A more preferred subclass of compounds of the Formula I includes compounds wherein X is hydrogen chloro, bromo, fluoro, methyl or methoxy and wherein $R^1$ and $R^2$ independently are isopropyl, cyclopentyl, cyclohexyl, methylcyclohexyl or dimethylcyclohexyl, and wherein Y and Y' are either both hydrogen or taken together are oxo (=O). Particularly preferred compounds of Formula I include:

cis-N-cyclopentyl-4-[(2,3-dihydro-1H-pyrido[3,4-b][1,4]-oxazin-1-yl)methyl-N-(3,5-dimethylcyclohexyl)-2-methoxybenzamide;

N-cyclohexyl-N-cyclopentyl-4-[(2,3-dihydro-1H-pyrido[3,4-b][1,4]oxazin-1-yl)methyl]-3-methylbenzamide;

3-bromo-N-cyclohexyl-4-[(2,3-dihydro-1H-pyrido[3,4-b][1,4]oxazin-1-yl)methyl]-N-(1-methylethyl)-benzamide; and N-cyclohexyl-4-[{2,3-dihydro-2-oxo-1H-pyrido(2,3-b)(1,4)oxazin-1-yl}methyl]-3-methoxy-N-(1-methylethyl)benzamide.

Included within the classes and subclasses of compounds embraced by Formula I are isomeric forms of the described compounds including diastereoisomers, enantiomers and tautomeric forms of the described compounds. Pharmaceutically acceptable salts of such compounds are also included as well as pharmaceutically acceptable salts of such isomers and tautomers.

In the structures herein a bond drawn across a bond in a ring indicates that the bond can be to any available atom of the ring structure.

The term "pharmaceutically acceptable salt," as used herein, refers to conventionally accepted pharmaceutical salts prepared by processes which are well known to those of ordinary skill in the art. [See for example, S. M. Berge, et al., "Pharmaceutical Salts," *J. Pharm. Sci.*, 66:1–19 (1977)].

The term "composition" as used herein means a product which results from the mixing or combining of more than one element or ingredient.

The term "pharmaceutically acceptable carrier" as used herein means a pharmaceutically-acceptable material, composition or vehicle, such as a liquid or solid filler, diluent, excipient, solvent or encapsulating material, involved in carrying or transporting a chemical agent.

The term "therapeutically effective amount" shall mean that amount of drug or pharmaceutical agent that will elicit the biological or medical response of a tissue, system or animal that is being sought by a researcher or clinician.

The term "alkyl" as used herein means a hydrocarbon (linear or branched) radical having from one to twelve carbon atoms, and more preferably from one to six carbon atoms. Representative of such radicals are methyl, ethyl, n-propyl, isopropyl, n-butyl, sec-butyl, isobutyl, tert-butyl, 2-ethylhexyl, n-octyl, 2,4-dimethylpentyl and the like.

The term "halogen" or "halo" as used herein means a fluoro, chloro, bromo or iodo radical.

The term amino denotes a radical of the formula —$NH_2$. The term "alkylamino" as used herein is represented by the radical —$NHR_5$ wherein $R_5$ is an alkyl group as previously described. The term "dialkylamino" as used herein is represented by the radical —$NR_6R_5$ wherein $R_6$ and $R_5$ are the same or different alkyl groups, as defined above. The term "aminoalkyl" as used herein is represented by the formula —$R_9NH_2$ wherein $R_9$ is an alkyl group as defined above. The term "alkylaminoalkyl" is represented by the formula —$R_9NHR_8$ wherein $R_8$ and $R_9$ are the same or different alkyl groups.

The term "haloalkyl" embraces radicals wherein any one or more of the alkyl carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group, such as monofluoromethyl. Dihaloalkyl and polyhaloalkyl groups may be substituted with two or more of the same halo groups, or may have a combination of different halo groups. A dihaloalkyl group, for example, may have two fluorine atoms, such as difluoromethyl and difluorobutyl groups, or two chloro atoms, such as dichloromethyl group, or one fluoro atom and one chloro atom, such as a fluorochloromethyl group. Examples of a polyhaloalkyl are trifluoromethyl, 1,1-difluoroethyl, 2,2,2,-trifluoroethyl, perfluoroethyl, 2,2,3,3-tetrafluoropropyl and perfluoropropyl groups. The term "difluoroalkyl" embraces alkyl groups having two fluorine atoms substituted on any one or two of the alkyl group carbon atoms.

The term "hydroxyalkyl"embraces linear or branched alkyl groups having one to about ten carbon atoms any one or more of which may be substituted with a hydroxyl group.

The term "alkylsilyloxyalkyl" embraces a silyloxyalkylene group wherein such group is attached to the nucleus of Formula I through its alkylene moiety and which group has three terminal alkyl moieties attached to the silyl portion of such group. Similarly, the term "aryl/alkylsilyloxyalkyl" embraces a silyloxyalkylene group wherein such group is attached to the nucleus of Formula I through its alkylene moiety and which group has three terminal moieties selected from alkyl and aryl, which three moieties are attached to the silyl portion of such group. Similarly, the term "arylsilyloxyalkyl" embraces a silyloxyalkylene group wherein such group is attached to the nucleus of Formula I through its alkylene moiety and which group has three terminal aryl moieties attached to the silyl portion of such group.

The term "alkenyl" embraces linear or branched hydrocarbon radicals having two to about twenty carbon atoms, preferably three to about ten carbon atoms, and containing at least one carbon-carbon double bond, which carbon-carbon double bond may have either cis or trans geometry within the alkenyl moiety, relative to groups substituted on the double-bonded carbons. The term "alkynyl" embraces linear or branched hydrocarbon radicals having two to about twenty carbon atoms, preferably two to about ten carbon atoms, and containing at least one carbon-carbon triple bond.

The term "cycloalkenyl" embraces cyclic radicals having three to about eight ring carbon atoms including one or more double bonds between adjacent ring carbons.

The terms "alkoxy" and "alkoxyalkyl" embrace linear or branched oxy containing radicals each having alkyl portions of one to about ten carbon atoms. An example of an alkoxy is a methoxy group. The term "alkoxyalkyl" further embraces alkyl radicals having two or more alkoxy groups attached to an alkyl radical.

The term "alkylthio"embraces radicals containing a linear or branched alkyl group, of one to about ten carbon atoms attached to a divalent sulfur atom, exemplified by a methylthio group. The terms "sulfinyl" and "sulfonyl", whether used alone or linked to other terms such as "alkyl", denote —SO— and —$SO_2$—,respectively.

The term "aryl" denotes a carbocyclic aromatic ring system composed of one or more aromatic rings. Preferred aryl groups are those consisting of one, two, or three benzene rings. The term "aryl" embraces aromatic radicals such as phenyl, naphthyl and biphenyl. The term "aralkyl" embraces aryl-substituted alkyl radicals such as benzyl, diphenylmethyl, triphenylmethyl, phenylethyl, phenylbutyl and diphenylethyl. The terms "benzyl" and "phenylmethyl" are interchangeable.

The term "amido" denotes a radical consisting of nitrogen atom attached to a carbonyl group, which radical may be further substituted in the manner described herein. The amido radical can be attached to the nucleus of a compound of the invention through the carbonyl moiety or through the nitrogen atom of the amido radical.

The term "cycloalkyl" embraces mono-carbocyclic saturated radicals having three to about eight ring carbon atoms, preferably three to about six carbon atoms, such as cyclopropyl, cyclobutyl, cyclopentyl and cyclohexyl. The term "cycloalkylalkyl" denotes a cycloalkyl radical attached to an alkyl radical which is attachable to a substitutable position of Formula I. Examples of "cycloalkylalkyl" radicals are cyclopentylmethyl and cyclohexylethyl. The term "alkylcycloalkyl" embraces cycloalkyl radicals substituted by an alkyl group as defined above.

The term "cycloalkylhaloalkyl" denotes a cycloalkyl radical attached to a carbon atom of a haloalkyl group as defined above.

The term "formyl" is represented by a radical of the formula —CHO.

The term "cycloalkylcarbonyl" embraces a cycloalkyl radical attached to a "carbonyl" radical of the formula

The term "arylalkylhaloalkyl," as used herein denotes an aralkyl radical as defined above attached via the alkyl portion of the radical to a carbon atom of a haloalkyl radical as defined above.

The term "haloaryl" embraces an aryl radical as defined above substituted on one or more of the ring carbon atoms by the same or different halo radicals as defined above.

The term "aroyl" as used herein denotes an aryl radical as defined above, attached via a ring atom to a carbonyl radical. Representative aroyl radicals include radicals such benzoyl and napthoyl.

The term "bicycloalkyl" as used herein denotes a fused ring system having two fused rings collectively composed of seven to about twelve carbon atoms.

The term "aryloxyalkyl" denotes an aryl radical as defined above attached via a divalent oxygen atom to an alkyl radical as defined above.

The term "alkylcarbonyl" as used herein, denotes an alkyl group as defined above attached to a carbonyl radical as defined above.

The term "alkylcarbonylalkyl" embraces a carbonyl radical as defined above with the same or different alkyl radicals, as defined above, attached to each of its two free valencies.

The term "alkoxycarbonyl" is represented by a radical of the formula —$COO_7$ wherein $R_7$ is an alkyl group as defined above.

The term "carboxyl" denotes a radical of the formula —COOH.

The term "carboxyalkyl," as used herein, denotes a radical of the formula —$R_7$COOH wherein $R_7$ is an alkyl group as defined above.

The term "alkylcarbonyloxyalkyl" is represented by a radical of the formula $R_8COOR_9$— wherein $R_8$ and $R_9$ are the same or different alkyl groups as defined above.

The term "alkoxycarbonylalkyl" is represented by a radical of the formula $R_{24}OC(O)R_{25}$— where $R_{24}$ and $R_{25}$ are the same or different alkyl groups as defined above.

The term "aralkoxycarbonylalkyl," as used herein is represented by a radical of the formula $R_{26}$—$R_{27}$—O—C(O)—$R_{28}$— wherein $R_{26}$ is an aryl group as defined above and $R_{27}$ and $R_{28}$ are the same or different alkyl groups as defined above.

The term "aralkylcarbonyloxyalkyl" denotes a radical of the formula $R_{29}$—$R_{30}$—COO—$R_{31}$— wherein $R_{29}$ is an aryl group as defined above and $R_{30}$ and $R_{31}$ are the same or different alkyl groups as defined above.

The term "mercaptoalkyl" as used herein is denoted by a radical of the formula HS—$R_{32}$— wherein $R_{32}$ is an alkyl group as defined above.

The term "alkylthioalkyl" as used herein denotes a radical of the formula $R_{35}$—S—$R_{36}$— wherein $R_{35}$ and $R_{36}$ are the same or different alkyl radicals as defined above.

Compounds of Formula I or their physiologically-acceptable or pharmaceutically-acceptable salts have PAF-antagonistic activity and are of potential value therapeutically as active components in pharmaceutical compositions. Platelet activating factor (PAF) is the phospholipid "1-0-alkyl-2-acetyl-sn-glycero-3-phosphocholine" (AGEPC) which is known as a potent lipid mediator released by animal and human proinflammatory cells. These cells include primarily basophilic and neutrophilic granulocytes, endothelial cells, fibroblasts, epithelial brain cells, macrophages (from blood and tissue) and thrombocytes which are involved in inflammatory reactions.

In pharmacological trials, PAF may cause bronchoconstriction, a lowering of blood pressure, the triggering of thrombocyte aggregation and a proinflammatory activity. Thus PAF is indicated, directly or indirectly, as a mediator in anaphylaxis, in the pathophysiology of allergic conditions, bronchial asthma and in inflammations in general. Compounds of Formula I are therefore suitable for treating patients affected by diseases in which PAF is implicated, including inflammatory or allergic processes or autoimmune diseases. Examples of indications for a PAF antagonist include inflammatory processes of the tracheobronchial tree (acute and chronic bronchitis, bronchial asthma) or of the kidneys (glomerulonephritis), the joints (rheumatic complaints), anaphylactic conditions, allergies and inflammation in the mucous membrances (rhinitis, conjunctivitis) and the skin (e.g. psoriasis, atopic eczema, cold-induced urticaria) and shock caused by sepsis, endotoxins, trauma or burns.

Other important indications for a PAF antagonist include the following: lesions and inflammation in the gastric and intestinal linings, such as shock ulcers, ulcerative colitis, Crohn's disease, ischemic bowel necrosis, stress ulcers and peptic ulcers in general, but particularly ventricular and duodenal ulcers; obstructive lung diseases such as bronchial hyper-reactivity; inflammatory diseases of the pulmonary passages, such as chronic bronchitis; cardio/circulatory diseases such as polytrauma; anaphylaxis and arteriosclerosis; inflammatory intestinal diseases, EPH gestosis (edema-proteinuria hypertension); diseases of extracorporeal circulation, e.g. heart insufficiency, cardiac infarct, organ damage caused by high blood pressure, ischemic diseases, inflammatory and immunological diseases; immune modulation in the transplanting of foreign tissues, e.g. the rejection of kidney, liver and other transplants; immune modulation in leukemia; propagation of metastasis, e.g. in bronchial neoplasia; diseases of the CNS, such as migraine, multiple sclerosis, endogenic depression and agoraphobia (panic disorder). Compounds of Formula I could also be effective as follows: as cyto- and organoprotective agents, e.g. for neuroprotection; to treat DIC (disseminated intravascular coagulation); to treat side effects of drug therapy, e.g. anaphylactoid circulatory reactions; to treat incidents caused by contrast media and other side effects in tumor therapy; to diminish incompatibilities in blood transfusions; to prevent fulminant liver failure ($CCl_4$ intoxication); to treat amanita phalloides intoxication (mushroom poisoning); to treat symptoms of parasitic diseases (e.g. worms); to treat autoimmune diseases (e.g. Werlhof's disease); to treat autoimmune hemolytic anemia, autoimmunologically induced glomerulonephritis, thyroids Hashimoto, primary myxedema, pernicious anemia, autoimmune atrophic gastritis, Addison's disease, juvenile diabetes, Goodpasture syndrome, idiopathic leucopenia, primary biliary cirrhosis, active or chronically aggressive hepatitis (HBsAg-neg.), ulcerative colitis and systemic lupus erythematodes (SLE), ideopathic thrombocytopenic purpura (ITP); to treat diabetes, juvenile diabetes, diabetic retinopathy, polytraumatic shock, haemorrhagic shock; and to treat PAF-associated interaction with tissue hormones (autocoid hormones), lymphokines and other mediators.

The compounds of the present invention can be administered in such oral dosage forms as tablets, capsules, softgels, pills, powders, granules, elixirs or syrups. The compounds can also be administered intravascularly, intraperitoneally, subcutaneously, intramuscularly or topically using forms known to the pharmaceutical art. Moreover, they can be administered rectally, in such forms as suppositories, enemas or bougies. In general the preferred form of administration is oral.

For the orally administered pharmaceutical compositions and methods of the present invention, the foregoing active ingredients will typically be administered in admixture with suitable pharmaceutical diluents, excipients or carriers (collectively referred to hereinafter as "carrier" materials). Such carrier materials are suitably selected with respect to the intended form of administration and consistent with conventional pharmaceutical practices.

For example, for oral administration in the form of tablets or capsules, a therapeutically effective amount of one or more compounds of the present invention can be combined with any oral pharmaceutically acceptable inert carrier such as lactose, starch, sucrose, cellulose, magnesium stearate, calcium sulfate and the like or various combinations thereof. For oral administration in liquid forms, such as in softgels, elixirs, syrups and the like, a therapeutically effective amount of the active drug components can be combined with any oral pharmaceutically acceptable inert carrier such as water, ethanol, polyethylene glycol, vegetable oils, propylene glycol, benzylalcohol and the like or various combinations thereof.

When desired or necessary, suitable binders, lubricants, disintegrating agents, preservatives, and coloring or flavoring agents can also be incorporated into the mixture. Suitable binders include starch, gelatin, natural sugars, corn sweeteners, natural and synthetic gums and waxes and the like, or combinations thereof. Lubricants can include boric acid, sodium benzoate, sodium acetate, sodium chloride and the like, or combinations thereof. Disintegrators include without limitation starch, methylcellulose, agar, bentonite, guar gum and the like, or combinations thereof.

For intravascular, intraperitoneal, subcutaneous or intramuscular administration, one or more compounds of the present invention can be combined with a suitable carrier such as water, saline, aqueous dextrose and the like. For topical administration therapeutically effective amounts of one or more compounds of the present invention can be combined with pharmaceutically acceptable creams, oils, waxes, gels and the like.

Regardless of the route of administration selected, a therapeutically effective amount of the compounds of the present invention are formulated into pharmaceutically acceptable dosage forms by conventional methods known to those skilled in the art. The dosage for preventing or treating PAF mediated conditions with the compounds of the present invention is determined in accordance with a variety of factors, including the type, age, weight, sex and medical condition of patient, the severity of the condition, the route of administration and the particular compound employed in the treatment. A physician or veterinarian of ordinary skill can readily determine and prescribe an effective amount of drug required to prevent or arrest progress of the condition. In so proceeding, the physician or veterinarian could employ relatively low doses at first and subsequently increase the dose until a maximum response is obtained. The daily doses of the compounds of the present invention are ordinarily in the range of about 0.5 mg to about 2000 mg, more preferably in the range of about 5 mg to about 1000 mg.

The compounds of this invention are generally prepared according to reaction schemes I-X.

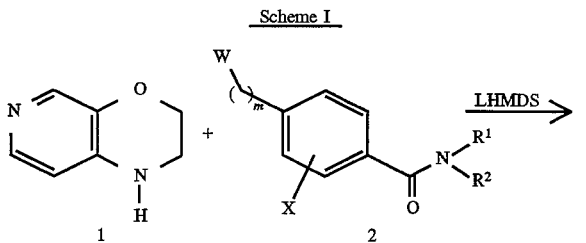

Scheme I

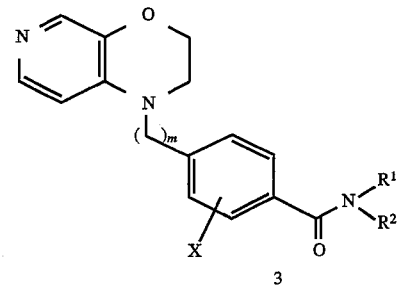

Scheme I depicts a presently preferred method for preparing compounds of the general Formula I (wherein A-B is —N═CH—). A solution of 2,3-dihydro-1H-pyrido-[3,4b][1,4]oxazine in a suitable solvent such as tetrahydrofuran is cooled to −70° C. in an argon atmosphere and an equimolar amount of a base such as lithium hexamethyldisilazide ("LHMDS") (also known as lithium bis(trimethylsilyl) amide) is injected into the reaction mixture and the resulting suspension is stirred for several minutes. To the stirred suspension is added dropwise a solution of a suitable haloalkylbenzamide 2 in an inert solvent such as THF. The reaction mixture is allowed to warm slowly from −70° C. to a temperature of from about 0° C. to about 40° C. and the reaction allowed to proceed from about 0.1 to about 5 hours to provide compound 3 which is a PAF antagonist of the present invention.

Scheme II shows the presently preferred method for preparing 2,3-dihydro-1H-pyrido-[3,4b][1,4]oxazine, compound 1, a starting material in the preparation of compounds of Formula I, wherein A-B is —N═CH—. With reference to Scheme II, 3-chloropyridine-N-oxide, 4, is prepared from the reaction of 3-chloropyridine with aqueous hydrogen peroxide in acetic acid at reflux temperatures. The N-oxide 4 is reacted with sodium methoxide in methanol in an argon atmosphere to produce the corresponding 3-methoxy compound 5, which may be isolated and crystallized by tituration with hexane. Compound 5 is then dissolved by careful addition of concentrated $H_2SO_4$ at 0° C. (ice bath) and fuming nitric acid is added slowly (with rapid stirring) to the solution and the reaction is allowed to proceed at about 75° C. for 2–3 hours to provide the corresponding 4-nitro compound 6, which is then hydrogenated with a catalytic amount of Raney Nickel to provide 4-amino-3-methoxy pyridine 7. Compound 7 is then treated with boron tribromide to provide 4-amino-3-hydroxy pyridine 8. The 4-amino moiety of compound 8 is converted to a chloroacetamido moiety by reaction with chloroacetyl chloride at reflux to provide compound 9 which is cyclized upon treatment with potassium carbonate to provide 1H-pyrido[3,4-b][1,4]oxazine-2-(3H) one. Reduction of compound 8 with borane/dimethylsulfide provides 2,3-dihydro-1H-pyrido[3,4-b][1,4]oxazine 1. Either compound 1 or 10 may be condensed with a substituted haloalkylbenzamide 2 to provide a PAF antagonist compound of Formula I wherein, A-B is —N═CH— and Y is hydrogen or ═O, as shown in Scheme I.

filtered and the filtrate concentrated in vacuo to give a crude product that is chromatographed on silica gel using mixtures of ethyl acetate and hexane to give the purified amide.

Where X is —OMe or —F, in order to properly introduce a leaving group, W, on the methyl group, compound 13 is halogenated with a halogenating agent such as N-bromosuccinimide. N-bromosuccinimide (NBS) may be added to a stirred mixture of the purified amide (1:1 molar ratio) in carbon tetrachloride. The reaction mixture is irradiated with a sun lamp (150 or 275 W) for 1–3 hours to give a white precipitate which may be filtered and washed with a minimum amount of $CHCl_3$. The filtrate is basified with ammonium hydroxide, washed with water, and the aqueous layer is extracted three times with chloroform. All organic layers are combined, washed three times with saturated aqueous sodium chloride solution and dried over sodium sulfate.

The drying agent is filtered and the filtrate concentrated in vacuo to give a crude product that is chromatographed on silica gel using mixtures of ethyl acetate and hexane to give the purified bromomethyl compound 14.

Where X is halogen, preferably bromine or fluorine, reacting amide 13 with a cyanide reagent such as cuprous cyanide, in a high boiling solvent, such as DMF or collidine, prior to treatment with NBS provides compound 14 wherein X is a cyano moiety.

SCHEME III

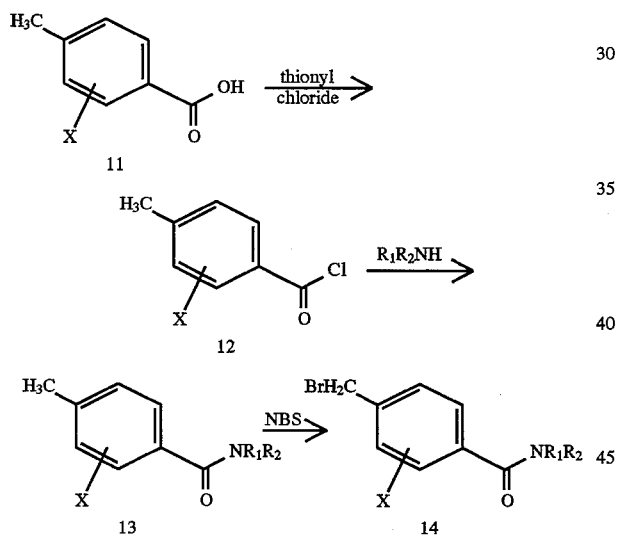

Scheme III shows a method for making haloalkylbenzamides wherein W is Br, m is 1 (see compound 2 in Scheme I), and X is hydrogen, halogen or alkoxy. Benzoic acid derivative 11 is converted to its corresponding acid chloride by treatment with excess chlorinating agent such as thionyl chloride at temperatures of from room temperature to reflux. Excess thionyl chloride is removed by azeotrope with toluene. The residual acid chloride 12 is dissolved in THF or other inert solvent and cooled to −10° C., and a solution of two molar equivalents of the secondary amine [$HN(R^1)(R^2)$], wherein $R^1$ and $R^2$ are defined herein, in THF is added dropwise with stirring. When addition is completed, the reaction is allowed to warm to room temperature and stirred for 1–2 hours to provide compound 13. The reaction is then quenched with 1N HCl, diluted with $H_2O$ and extracted three times with ethyl acetate, and the combined organic layers are washed with saturated aqueous sodium bicarbonate solution, with water and with saturated aqueous sodium chloride and dried over sodium sulfate. The drying agent is

SCHEME IV

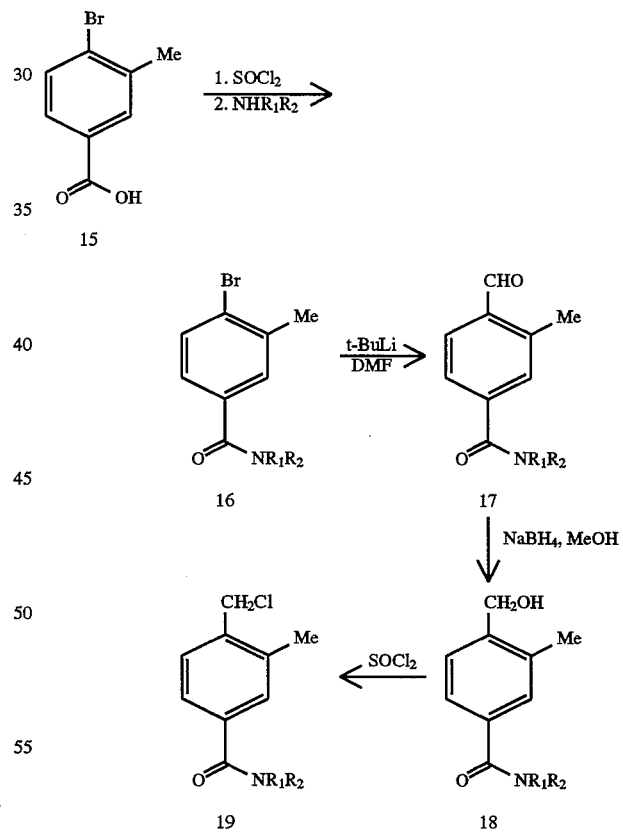

Scheme IV depicts a presently preferred method for preparing haloalkylbenzamides 2 (see Scheme I) wherein W is Cl, m is 1, and X is alkyl. The benzoic acid derivative 19 may be synthesized by converting 4-bromo-methyl-benzoic acid 15 to its corresponding benzamide derivative 16 by reaction with an appropriate chlorinating agent such as thionyl chloride to form the acid chloride of 15 (not shown), followed by reaction, in THF or other suitable inert solvent, of the acid chloride with a predetermined secondary amine (wherein $R^1$ and $R^2$ are defined above) as shown in Scheme II. The bromobenzamide derivative 16 is then treated with an organometallic reagent such as t-butyl lithium and reacted with an electrophile such as dimethylformamide to provide aldehyde 17, which is reduced to alcohol 18 with sodium borohydride or other suitable reducing agent in the presence of methanol. Alcohol 18 is treated with thionyl chloride to provide the corresponding chloromethyl benzamide 19, which may be utilized in the synthesis depicted in Scheme I to provide compounds of Formula I.

3327(1974), by reaction with carbon monoxide in the presence of bistriphenylphosphine palladium(II) dibromide as the catalyst and employing the desired secondary amine ($HNR^1R^2$) as solvent. The reaction may be carried out at about 100° C. for 8–26 hours in a pressure vessel. The reaction vessel is vented, the reaction mixture triturated with ethyl ether and the washings filtered. The filtrate is washed with 10% aqueous HCl, water and brine. After drying over a suitable drying agent, such as magnesium sulfate, and filtering, the filtrate is concentrated and the residue chromatographed on silica gel using mixtures of ethyl acetate

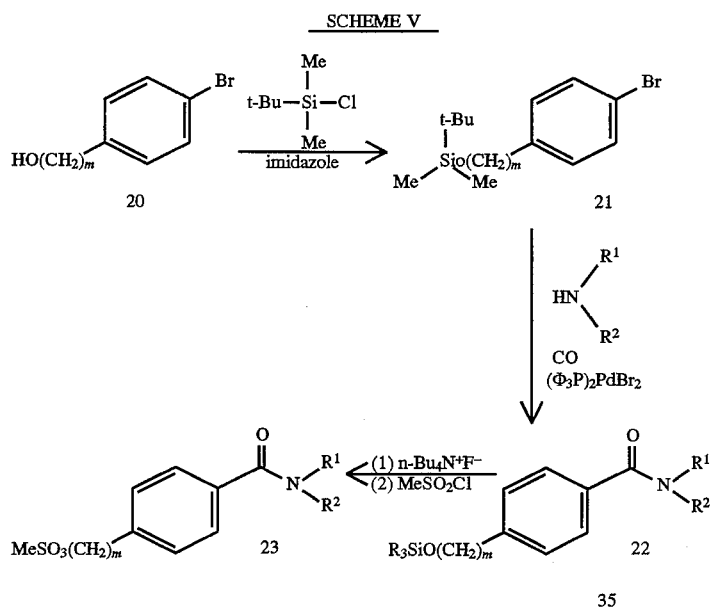

SCHEME V

Scheme V shows a method for preparing alkylbenzamides 23, wherein m is 2 or 3, and the leaving group W (See Scheme I) is a methylsulfonate ester. With reference to Scheme V, a suitable hydroxyalkyl bromobenzene 20 is silylated to protect the hydroxyl group of compound 20 with a suitable silylating agent such as t-butyldimethylsilyl chloride in the presence of imidazole in a suitable solvent such as dimethylformamide. The silylated aryl bromide 21 is converted to its corresponding carboxamide 22 according to the procedure of Schoenberg et al., J. Org. Chem., 39, and hexane as eluent to give pure product. The silyl ether moiety of compound 22 is removed by reaction with tetra-n-butylammonium fluoride to provide the corresponding alcohol (not shown), and the alcohol is converted to sulfonate ester 23 by reaction with methanesulfonyl chloride or other suitable alkyl or arylsulfonyl chloride.

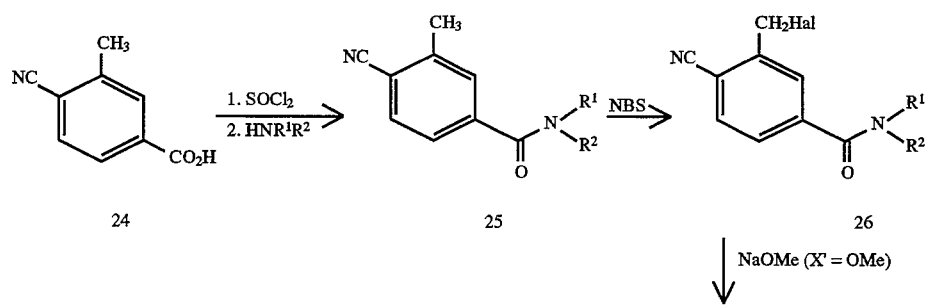

SCHEME VI

-continued
SCHEME VI

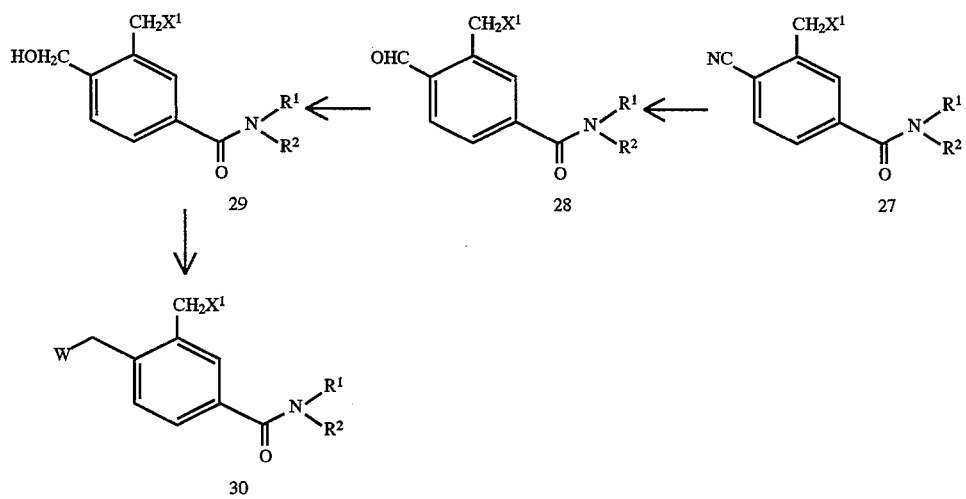

Scheme VI shows a general method for the preparation of substituted benzamide compounds of the general formula

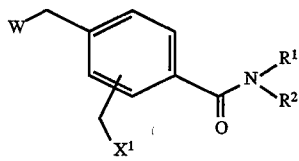

wherein $X^1$ is alkoxy, alkylthio, amino, alkylamino or dialkylamino; W is chloro, bromo, alkanesulfonyloxy, arylsulfonyloxy or p-toluenesulfonyloxy; and $R_1$ and $R_2$ are defined as before. The term "Hal" as used in Scheme VI and the description thereof, means halogen.

Where $X^1$ is alkoxy (i.e., the substituent X of Formula I is alkoxymethyl) introduction of the alkoxy moiety may be accomplished using a presently preferred method which employs methyl substituted 4-cyanobenzoic acid, for example, 4-cyano-3-methyl benzoic acid 24 (see, F. Fichter, G. Shetty, Helv. Chim. Acta, 20, 563 (1937)) as starting material. Compound 24 is converted to the appropriate amide by conversion to the acid chloride with oxalyl chloride, thionyl chloride or other suitable halogenation reagent. Contacting the acid chloride with the appropriate amine provides the desired benzamide 25, which is then treated with a brominating agent such as N-bromosuccinimide to yield the methyl-substituted 4-cyanobenzamide 26. It should be appreciated by the art-skilled that compound 26 is a versatile intermediate which may be used to provide a variety of compounds 2 wherein X is alkoxyalkyl, alkylthioalkyl, alkylaminoalkyl, and the like, by treatment of compound 26 with a suitably reactive derivative of X'. Thus, for example, where the halogen atom ("Hal" of compound 26) is displaced with a metal alkoxide, such as sodium methoxide, the methoxymethyl derivative 27 (X' is OMe) is obtained. Analogously, it will be understood by the art-skilled that displacement of "Hal" with (i) ammonia, (ii) a primary amine or (iii) a secondary amine, respectively, provides the corresponding compound wherein the substituent X is aminomethyl, alkylaminomethyl or dialkylaminomethyl. Alternatively, "Hal" may be displaced with a metal salt of the anion of ammonia, a primary or a secondary amine to produce the same products.

Moreover, it will be appreciated that the halogen (i.e., "Hal") may also be displaced with a metal alkylmercaptide, such as sodium methyl mercaptide, to provide the corresponding alkylthiomethyl-substituted compound.

Conversion of compound 27 to the aldehyde 28 may be effected by controlled reduction with a reducing agent such as diisobutylaluminum hydride, followed by acid hydrolysis. Reduction of aldehyde 28 to the alcohol 29 may be carried out by a second reduction step utilizing a reducing agent such as sodium borohydride or lithium tri-t-butoxyaluminum hydride. Alcohol 29 is converted to compound 30 suitable for nucleophilic displacement wherein W is a leaving group such as a halide atom, or aryl sulfonate or alkyl sulfonate moiety by treatment of the alcohol with, for example, thionyl chloride as depicted in Scheme III, p-toluenesulfonyl chloride, methanesulfonyl chloride as shown-in Scheme VI, or the like.

Still other haloalkylbenzamides which may be used in the preparation of the compounds of the present invention are disclosed in WO 89/08653 and U.S. Pat. No. 5,019,581, which are incorporated herein by this reference.

A wide variety of secondary amines (sec-amines) of the formula $HNR^1R^2$ are commercially available or may be prepared by known methods which are routine to those having ordinary skill in the art and utilized as intermediates in the preparation of alkylbenzamide derivatives as shown in Schemes III through VI. Methods for the preparation of amines, including secondary amines, are well known and described in the literature. See, for example, Emerson, W. S. Org. Reactions 4, 174 (1948); and J. B. Campbell, L. B. Lavaginino in "Catalysis in Organic Syntheses" (Jones W. H., ed.) p. 43, Academic Press, New York, 1980.

A presently preferred method for preparing sec-amines is reductive amination entailing reacting a primary amine and a ketone/aldehyde in a suitable solvent and at a pressure of between about 1 and about 10 atmospheres of hydrogen in the presence of a hydrogenation catalyst such as palladium on carbon, as depicted in the following Scheme. The reaction is preferably carried out at a temperature of from about 25° C. to about 50° C. or more until completion.

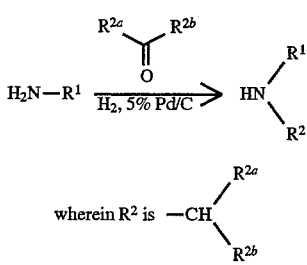

and $R^{2a}$ and $R^{2b}$ are independently hydrogen or alkyl, and $R^{2a}$ and $R^{2b}$ may be optionally linked so that —$CHR^{2a}R^{2b}$ is cycloalkyl.

By way of illustration, N-cis,cis-3,5-dimethylcyclohexyl-N-cyclopentylamine may be synthesized as shown in Scheme VII.

SCHEME VII

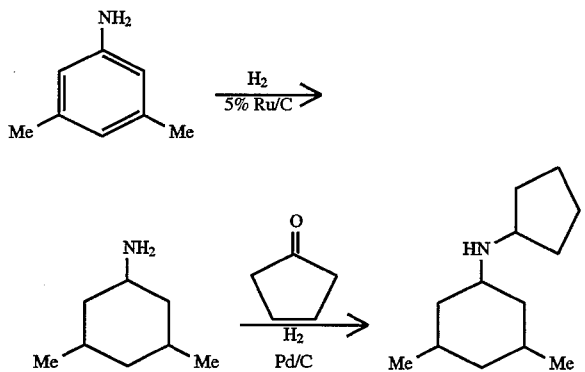

The primary amine, 3,5-dimethylcyclohexylamine, is prepared by catalytic hydrogenation of a 3,5-dimethyl aniline for 7 to 24 hours with a suitable hydrogenation catalyst such as 5% ruthenium on carbon at a pressure of from about 500 to 1500 psi and a temperatures of from about 80° to 150° C. N-cis, cis-3,5-Dimethylcyclohexyl-N-cyclopentyl amine is formed by reductive amination of cyclopentanone with 3,5-dimethylcyclohexyl amine. The reductive amination may be carried out by hydrogenation using palladium on carbon as a catalyst at pressures ranging from 15 to 90 psi. The temperature may range from room temperature to 50° C. The reaction time may be from about 7 to 48 hours.

SCHEME VIII

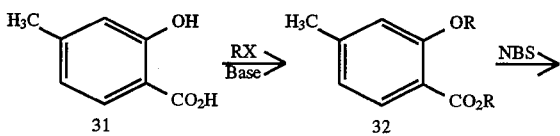

-continued
SCHEME VIII

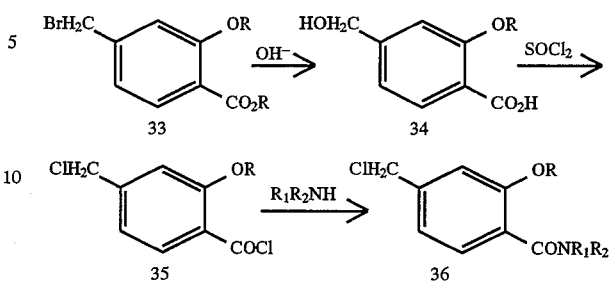

Scheme VIII shows an alternative and preferred method of synthesis of haloalkylbenzamides 2 wherein W is Cl, m is 1, and X is alkoxy. 2-Alkoxy-4-chloromethylbenzamides 36 may be synthesized from 2-hydroxy-4-methylbenzoic acid 31. Substituted benzoic acid 31 may be readily converted to its corresponding 2-alkoxy ester 32 using an alkyl halide such as methyl iodide (i.e., RX is $CH_3I$) in the presence of a base such as potassium carbonate. The reaction is conveniently carried out in a solvent such as dimethylformamide at a temperature of from about room temperature to about 60° C. The methyl group of ester 32 may then be brominated by free radical bromination using N-bromosuccinimide and illuminating the reaction mixture with a sun lamp capable of generating free radicals to provide 4-bromomethyl carboxylic acid ester 33. The ester 33 may be saponified to the corresponding acid with concomitant displacement of the benzylic bromide using a base such as potassium hydroxide in water at temperatures ranging from about 80° to $\leq 100°$ C. to give the 2-alkoxy-4-hydroxymethyl benzoic acid 34. An organic co-solvent such as dioxane or tetrahydrofuran may be used in order to facilitate dissolution of the organic substrate. Alternatively, compound 34 may be synthesized from bromide 33 in two steps by (1) reaction with a metal carboxylate such as sodium acetate or sodium benzoate in an inert solvent such as dimethylformamide, followed by (2) reaction with potassium hydroxide or other suitable base in an aqueous solvent such as aqueous ethanol or aqueous tetrahydrofuran. Compound 34 is converted to the 4-chloromethyl-2-alkoxybenzoyl chloride 35 by reaction with thionyl chloride at temperatures of from about room temperature to about 79° C. The alkoxy-substituted haloalkylbenzamide 36 is produced by reacting compound 35 with an predetermined secondary amine $HNR^1R^2$ in a solvent such as tetrahydrofuran at a temperature of from about 0° C. to about 60° C., and in the presence of a tertiary amine such as triethylamine to act as a hydrochloric acid scavenger.

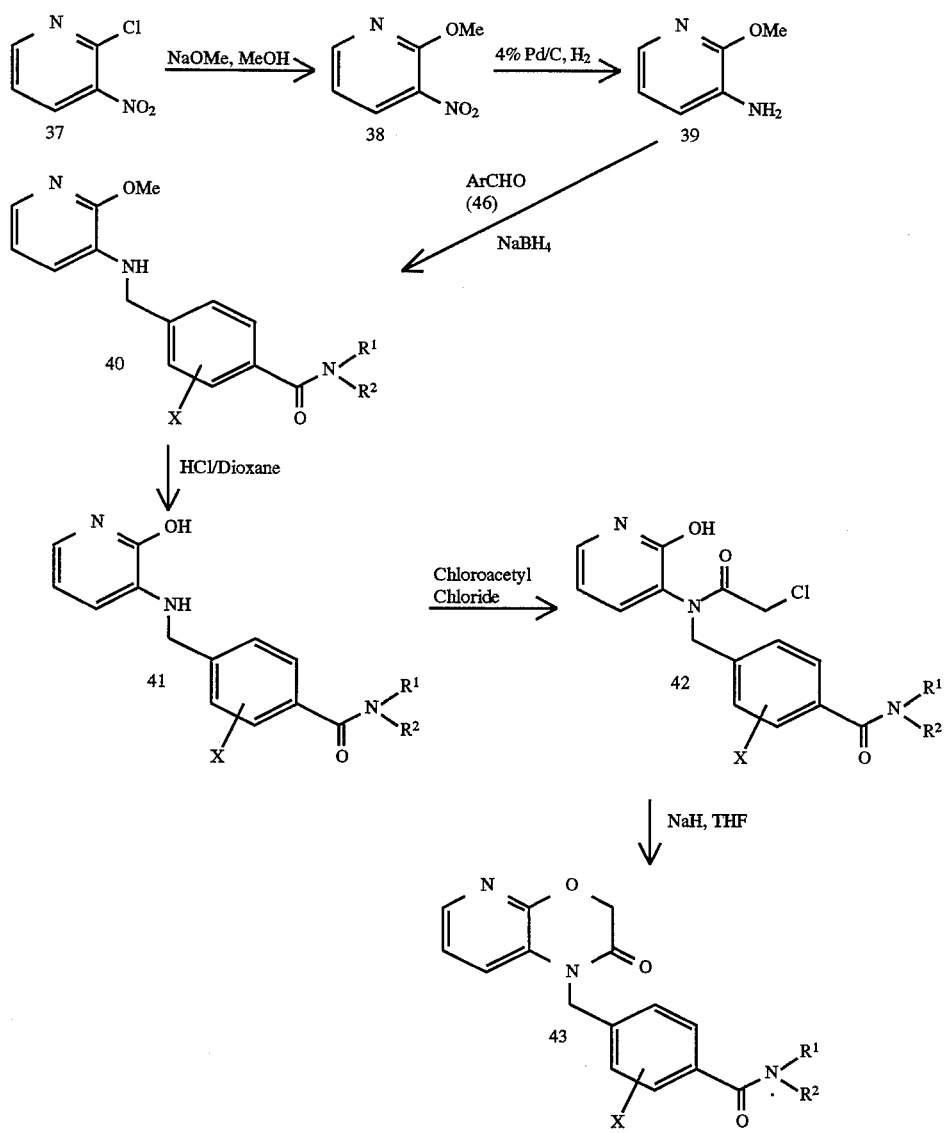

Scheme IX shows the presently preferred method of synthesis for compounds of Formula I where A-B is —CH=N—. 2-chloro-3-nitropyridine is suspended in methanol and reacted with 2 molar equivalents of sodium methoxide at reflux temperature to provide 2-methoxy-3-nitropyridine 38, which is precipitated by diluting the reaction mixture with about 4 volumes of water (with respect to the reaction mixture volume) to provide compound 38 as a white solid. Compound 38 is then dissolved in ethanol and hydrogenated over palladium on carbon to provide compound 39, which is concentrated from the reaction solution and reacted with arylaldehyde 46 in benzene at reflux for about 3 to 5 hours or more in the presence of a molecular seive having a pore size preferably about 4 Angstroms in diameter. (The synthesis of arylaldehyde 46 is described hereafter with reference to Scheme X.) The reaction mixture is then cooled to room temperature and stirred for about 12 to about 24 hours and then filtered and dried under vacuum. The crude dried product is dissolved in ethanol and treated with sodium borohydride for between about 18 and about 36 hours, cooled to room temperature and quenched with water. The aqueous solution of compound 40 is then extracted with methylene chloride, filtered and concentrated. Compound 40 is then treated with hydrochloric acid in dioxane to provide 41. Compound 41 is suspended in THF/ether (⅓) and chloroacetyl chloride is added and the resulting mixture is stirred at room temperature to provide compound 42. Treatment of compound 42 in THF with sodium hydride provides 43 which is a compound of Formula I, wherein A-B is —CH=N—.

Scheme X

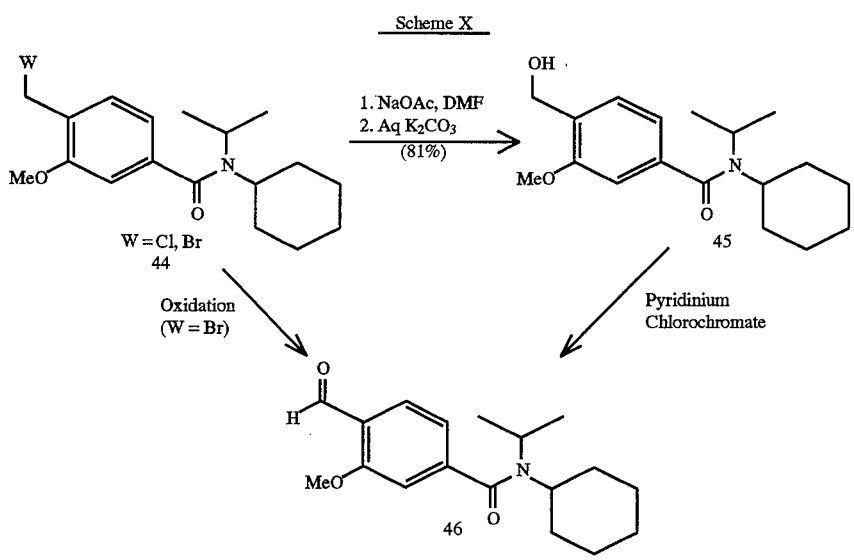

Scheme X depicts the synthesis of arylaldehydes (ArCHO) 46, which are useful reactants in the method depicted in Scheme IX. Halomethylbenzamides may be prepared as described herein with reference to any of Schemes III through V. By way of example, haloalkylbenzamide 44 in DMF is treated with sodium acetate at 80° C.–85° C. for about 4–8 hours and cooled to room temperature and stirred overnight. The reaction mixture is then treated with saturated aqueous potassium carbonate and stirred at room temperature for one to two days or more to provide the 4-hydroxymethyl compound 45. A solution of compound 45 in methylene chloride is then added to a suspension of pyridinium chlorochromate in methylene chloride and the reaction is carried out with stirring for about 2–3 hours to provide arylaldhyde 46.

The following examples illustrate the methods used to prepare the compounds of this invention. These Examples are given by way of illustration only and are not meant to be construed as limiting the invention in spirit or scope as many modifications in materials and methods will be apparent from this disclosure to one having ordinary skill in the art.

EXAMPLE 1

3-Chloropyridin-N-oxide

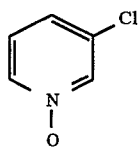

A solution of 3-chloropyridine (89.7 g, 0.79 mol) and 30% aqueous $H_2O_2$ (135 ml) in HOAc (800 ml) was refluxed for 4 hrs. and then stirred overnight at 25° C. The reaction mixture was evaporated on the rotary evaporator using an oil pump to give an oily residue that was further heated at 60° C. under high vacuum for 1 hour. Upon cooling to 4° C., the oily residue crystallized. The crystalline mass was triturated with ether, filtered and air dried to give 60 g (60%) of the titled product, m.p. 87°–88° C. The structural assignment is supported by the proton NMR spectrum.

Anal. calcd. for $C_5H_4ClNO$: C, 46.36; H, 3.11; N, 10.81; Cl, 27.37. Found: C, 46.11; H, 3.08; N, 10.45; Cl, 27.11.

EXAMPLE 2

3-Methoxypyridine-N-oxide

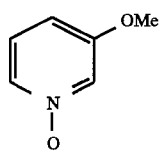

A solution of 3-chloropyridine-N-oxide (5.3g, 40 mmol) and 25% NaOMe in MeOH (25 ml) was refluxed for 24 hours under an argon atmosphere. The solvent was removed under reduced pressure and the residue was treated with $CH_2Cl_2$ and water. The organic phase was separated and dried ($Na_2SO_4$) and the solvent removed to give a residue which was triturated with hexane to yield 4 g (78%) of product as a crystalline solid, m.p. 99°–101° C. The structural assignment is supported by the proton NMR spectrum.

Anal. calcd. for $C_6H_7NO_2$: C, 57.59; H, 5.64; N, 11.19. Found: C, 57.48; H, 5.70; N, 11.02.

EXAMPLE 3

3-Methoxy-4-nitropyridine-N-oxide

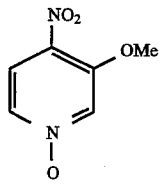

A solution of 3-methoxypyridine-N-oxide (24 g, 0.19 mol) and con. $H_2SO_4$(45 ml)was carefully prepared by adding the acid slowly to the solid N-oxide using an ice bath for cooling. After solution is effected, it is rapidly stirred and fuming nitric acid (45 ml) is added over 15 min. The reaction mixture was warmed to 75° C. for 2.5 hours. The contents were poured onto ice and neutralized to pH 9 with cooling using 50% NaOH. The mixture was extracted three times with CH$_2$Cl$_2$, dried, (Na$_2$SO$_4$) and solvent evaporated under reduced pressure to produce an oil. The crude product was chromatographed on silica gel using CH$_2$Cl$_2$/MeOH (99:1) as the eluent to give 17.5 g (41%) of the pure product as a crystalline solid, m.p. 125°–127° C. The structural assignment is supported by the proton NMR spectrum.

Anal. calcd for C$_6$H$_6$N$_2$O$_4$: C, 42.36; H, 3.55; N,16.47. Found: C, 42.14; H, 3.52; N, 16.37.

EXAMPLE 4

4-Amino-3-methoxypyridine

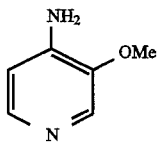

A solution of 3-methoxy-4-nitropyridine-N-oxide (17.37 g, 0.102 mol) in MeOH (180 ml) was hydrogenated in a 500 ml Parr bottle at 40° C. and 40 psi for 3 hours using Raney Nickel as catalyst. After filtration of the catalyst and evaporation of the solvent, the residue was chromatographed on silica gel using CH$_2$Cl$_2$/MeOH/NH$_4$OH (90/10/1) as the eluent to give the title compound. The product was recrystallized from toluene to give 10.8 g (65%) of pure product, m.p. 94°–95° C. The structural assignment is supported by the proton NMR spectrum.

Anal. Calcd. for C$_6$H$_8$N$_2$O: C, 58.05; H, 6.50; N, 22.57. Found: C, 58.09; H, 6.64; N, 22.48.

EXAMPLE 5

4-Amino-3-hydroxypyridine

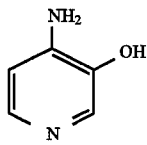

A solution of 3-methoxy-4-aminopyridine (200 mg, 1.6 mmol) in CH$_2$Cl$_2$ (15 ml) was stirred at −70° under an argon atmosphere. A solution of boron tribromide (10 ml of a 1M solution in CH$_2$Cl$_2$, 6 eq.) was added slowly over 10 minutes. After stirring in the cold for 15 min., the reaction mixture was allowed to warm to room temperature and stirred overnight. The solvent was removed under reduced pressure and the residue was stirred with MeOH and saturated NaHCO$_3$ for 25 minutes. The mixture was filtered and the filtrate was evaporated. The residue was stirred with CH$_2$Cl$_2$/MeOH/NH$_4$OH (75/25/2), filtered, and passed through a silica gel column, eluting with the same solvent mixture to give 145 mg (81%) of the desired product, m.p. 188°–191° C. The structural assignment is supported by the proton NMR spectrum.

Anal. Calcd. for C$_5$H$_6$N$_2$O·0.2 H$_2$O: C, 52.81; H, 5.67; N, 24.63. Found: C, 53.02; H, 5.63; N, 24.40.

EXAMPLE 6

4-Chloroacetamido-3-hydroxypyridine

A solution of 4-amino-3-hydroxypyridine (7 g, 0.06 mol) and chloroacetyl chloride (50 ml) was refluxed for 2 hours, cooled and the excess solvent was removed by vacuum distillation. The crude material was dissolved in water, neutralized with Na$_2$CO$_3$ and the solid precipitated filtered and air dried to give the desired product, m.p. 155°–158° C. The structural assignment was supported by the proton NMR spectrum.

EXAMPLE 7

1H-Pyrido[3,4-b][1,4]oxazine-2-(3H)one

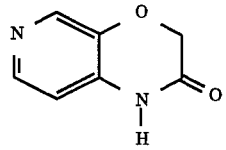

A solution of crude 4-chloroacetamido-3-hydroxypyridine (10 g, 0.05 mol) and potassium carbonate (10 g) in water (100 ml) was stirred at 25° C. overnight. The water was removed under vacuum using an oil pump at t<40° C. The residue was treated with MeOH and filtered. The filtrate was concentrated in vacuo and the residue treated with hot ethyl acetate and filtered. Upon cooling, the product precipitated from the filtrate to give 4.4 g (43% from 4-amino-3-hydroxypyridine), m.p. 203°–204° C. The structural assignment is supported by the proton NMR spectrum.

Anal. calcd. for C$_7$H$_6$N$_2$O$_2$·0.5 H$_2$O: C, 52.83; H, 4.43; N, 17.60. Found: C, 53.02; H, 4.19; N, 17.55.

EXAMPLE 8

2,3-Dihydro-1H-pyrido[3,4-b][1,4]oxazine

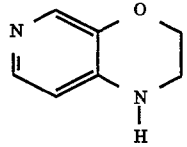

To a stirred solution of 1H-pyrido-[3,4-b][1,4]oxazine-2-(3H)one (3 g, 21 mmol) in tetrahydrofuran (150 ml) was added rapidly a borane/dimethyl sulfide solution (52 ml of a 2M solution in THF, 5 eq) at 25° C. over 15 minutes. The reaction mixture was stirred at 25° C. for 2 hours and quenched with 5 ml of water. The solvent was removed in vacuo using a rotary evaporator and the residue treated with aqueous 1M HCl with stirring. The water was removed and the residue chromatographed on silica gel using CH$_2$Cl$_2$/MeOH/NH$_4$OH (90/10/1) to give 2 g (70%) of titled product, m.p. 167°–169° C. The structural assignment is supported by the proton NMR spectrum.

Anal. calcd for $C_7H_8N_2O \cdot 0.25\ H_2O$: C, 58.80, H, 6.19; N, 18.34. Found: C, 58.80; H, 6.15; N, 18.55.

EXAMPLE 9

Cis-N-cyclopentyl-4-[(2,3-dihydro-1H-pyrido[3,4-b]
-[1,4]-oxazin-1-yl)methyl-N-[3,5-
dimethylcyclohexyl)-2-methoxybenzamide

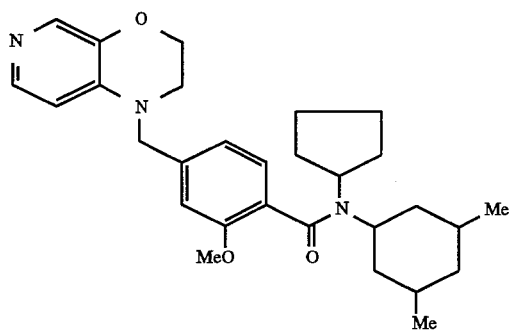

A solution of 2,3-dihydro-1H-pyrido-[3,4b][1,4]oxazine (138 mg, 1 mmol) in dry tetrahydrofuran (10 ml) was cooled to −70° C. under an argon atmosphere and a solution of lithium hexamethyldisilazide in THF (1 ml of a 1M solution, 1 eq) was added to the reaction mixture using a syringe. The resulting suspension was stirred for 10 minutes at −70° C. and a solution of 4-bromomethyl-3-methoxybenzoic acid-N-3,5-dimethylcyclohexyl, N-cyclopentyl amide (422 mg, 1 mmol) in THF (2 ml) was added over 3 minutes at −70° C. The reaction was allowed to warm slowly to 0° C. over 30 minutes and quenched by pouring the mixture into saturated $NaHCO_3$ solution (25 ml). The aqueous mixture was extracted with ethyl acetate, dried ($Na_2SO_4$) and the solvent removed to give the crude product. The residue was chromatographed on silica gel using ethyl acetate/MeOH/$NH_4OH$ (90/10/1) as the eluent and the isolated product recrystallized from ethyl acetate to give 56 mg (12%) of the titled compound, m.p. 180°–181° C. The structural assignment is supported by the proton NMR spectrum.

Anal. calcd. for $C_{29}H_{39}N_3O_3 \cdot H_2O$: C, 69.64; H, 8.36; N, 8.40. Found: C, 69.90; H, 8.07; N, 8.37.

EXAMPLE 10

N-cyclohexyl-N-cyclopentyl-4-[(2,3-dihydro-1H-
pyrido[3,4-b][1,4]oxazin-₁-yl)methyl]-3-methyl-
benzamide

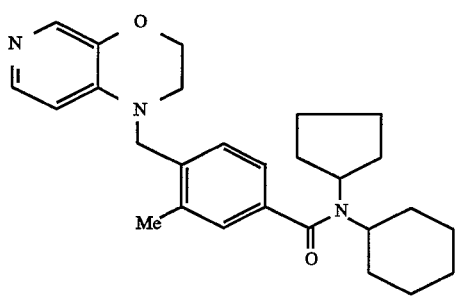

To a cold (−70°), stirred solution of 2,3-dihydro-1H-pyrido[3,4-b][1,4]oxazine (290 mg, 2 mmol) and 1,3-dimethyl-3, 4, 5, 6-tetrahydro-2(1H)-pyrimidinone (DPU) (3 ml) in dry THF (10 ml) was added a solution of lithium hexamethyldisilazide (2 ml of a 1M solution in THF, 1 eq). The reaction solution was stirred for 10 minutes and a solution of 4-chloromethyl-3-methylbenzoic acid N-cyclopentyl, N-cyclohexyl amide (720 mg, 2 mmol) in THF (10 ml) was added. The reaction was warmed to 40° C. for 5 hours. The reaction mixture was quenched by addition of a few drops of water. The solvent was removed under reduced pressure using a rotary evaporator. The residue was dissolved in ethyl acetate, washed three times with water to remove the DPU and the solution dried ($Na_2SO_4$). The drying agent was filtered and the filtrate concentrated in vacuo to give the crude product. Purification was carried out by chromatography on silica gel using $CH_2Cl_2$/MeOH/$NH_4OH$ (95/5/0.5) as the eluent to give the title compound. After recrystallization from ethyl acetate, there was obtained 200 mg (46%) of pure product, m.p. 207°–209° C. The Structural assignment is supported by the proton NMR spectrum.

Anal. calcd. for $C_{27}H_{35}N_3O_2 \cdot 0.25\ H_2O$: C, 74.02; H, 8.17; N, 9.59. Found: C, 73.81; H, 8.04; N, 9.84.

EXAMPLE 11

3-bromo-N-cyclohexyl-4-[(2,3-dihydro-1H-pyrido[3,
4-b]-[1,4]oxazin-1-yl)methyl]-N-(1-methylethyl)
benzamide

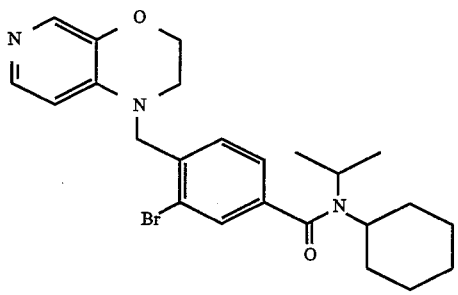

To a cold (−70°), stirred solution of 2,3-dihydro-1H-pyrido[3,4-b][1,4]oxazine (290 mg, 2 mmol) and 1,3-dimethyl-3, 4, 5, 6-tetrahydro-2(1H)-pyrimidinone (DPU) (3 ml) in dry THF (10 ml) was added a solution of lithium hexamethyldisilazide (2 ml of a 1M solution in THF, 2 mmol). The reaction solution was stirred for 10 minutes and a solution of of 4-bromomethyl-3-bromobenzoic acid-N-cyclohexyl, N-isopropyl amide contaminated with 4-methyl-3-bromobenzoic acid-N-cyclohexyl, N-isopropyl amide (1.1 g of approx. 75% pure bromide, approximately 2 mmol) in THF (10 ml) was added. The reaction was warmed to 40° C. for 5 hours. The reaction mixture was quenched by addition of a few drops of water. The solvent was removed under reduced pressure using a rotary evaporator. The residue was dissolved in ethyl acetate, washed three times with water to remove the DPU and the solution dried ($Na_2SO_4$). The drying agent was filtered and the filtrate concentrated in vacuo to give the crude product. Purification was carried out by chromatography on silica gel using $CH_2Cl_2$/MeOH/$NH_4OH$ (95/5/0.5) as the eluent to give 50 mg of the title compound, m.p. 191°–192°.

Anal. calcd. for $C_{24}H_{30}BrN_3O \cdot 0.25\ H_2O$: C, 60.44; H, 6.45; N, 8.81; Br, 16.75. Found: C, 60.05; H, 6.51; N, 8.67; Br, 16.41.

EXAMPLE 12

Synthesis of 2-methoxy-3-nitropyridine

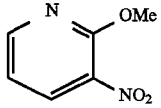

2-Chloro-3-nitropyridine (25 g, 0.157 mol) was suspended in methanol (300 ml) and sodium methoxide (17 g, 0.315 mol) was added. The mixture was refluxed for 2 hr and part of the solvent removed under reduced pressure. The reaction mixture was diluted with water (1 litre) and the precipitate collected by filtration. The white solid obtained was washed with more water and dried under vacuum to give the title compound (18.2 g, 75%). $^1$H NMR (CDCl$_3$): 8.42 (dd, J=5, 2 Hz, 1H); 8.28 (dd, J=8, 2 Hz, 1H); 7.06 (dd, J=8, 5 Hz, 1H); 4.13 (s, 3H)

EXAMPLE 13

Synthesis of 2-methoxy-3-aminopyridine

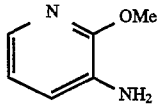

To a solution of the compound of Example 12 (17.12 g, 0.11 mol) in ethanol (180 mL) in a Parr bottle, was added 4% Pd/C (3.43 g). The bottle was sealed, purged with nitrogen and was pressurized (5 psi) with hydrogen. After stirring at room temperature for 2 hr, the reaction vessel was vented, purged with nitrogen and filtered. The clear filtrate was concentrated to give the title compound (15.3 g, 90%). $^1$H NMR (CDCl$_3$): 7.58 (dd, J=5, 2 Hz, 1H); 6.87 (dd, J=8, 2 Hz, 1H); 6.72 (dd, J=8, 5 Hz, 1H); 3.98 (s, 3H).

EXAMPLE 14

Synthesis of N-cyclohexyl-3-methoxy-4-[{(2-methoxy-3-pyridinyl)amino}methyl]-N-(1-methylethyl)-benzamide

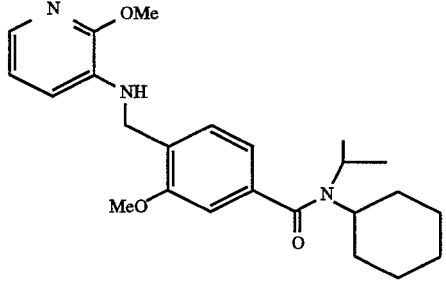

A suspension of molecular sieves (6 g, 4 A°) in a solution of the compound of Example 13 (904 mg, 7.3 mmol) and the aldehyde of Example 19 (2.6 g, 8.58 mmol) in benzene (150 ml) was refluxed with stirring for 3.5 hr. The reaction was cooled to room temperature and stirred for 18 hr. The reaction was filtered and the filter cake washed with ether (200 ml). The combined organic filtrates were concentrated and dried under vacuum. The crude dried product (3.6 g) was dissolved in ethanol (100 ml) and treated with sodium borohydride (4 g). After refluxing for 28 hr, the reaction mixture was cooled to room temperature and quenched with water (350 ml). The aqueous solution was extracted with methylene chloride (3×250 ml), dried (MgSO$_4$), filtered and concentrated. The crude product (3.23 g) was chromatographed (silica gel, ethyl acetate/acetone 98/2) to give 4 (2.4 g, 80%), m.p. (DSC) 187° C.

Anal calcd. for C$_{24}$H$_{33}$N$_3$O$_3$·0.4 H$_2$O: C, 68.84; H, 8.14; N, 10.03. Found: C, 68.87; H, 8.03; N, 9.94.

EXAMPLE 15

Synthesis of N-cyclohexyl-3-methoxy-4-[{(2-hydroxy-3-pyridinyl)amino}methyl]-N-(1-methylethyl)-benzamide

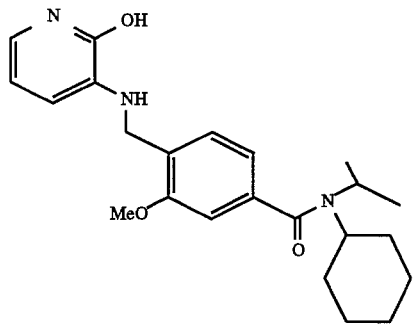

solution of compound of Example 14 (1.01 g, 2.04 mmol) in a 4M solution of dry HCl in dioxane (18 ml) was stirred at room temperature for 16 hr. The solvent was removed and the crude product treated with dilute aqueous ammonium hydroxide. Chromatography (silica gel, ethyl acetate/ acetone 98/2) of the crude product gave the title compound (780 mg, 96%).

Anal calcd. for C$_{23}$H$_{31}$N$_3$O$_3$·0.25 H$_2$O: C, 68.72; H, 7.90; N, 10.45. Found: C, 68.71; H, 8.07; N, 9.92.

EXAMPLE 16

Synthesis of 4-[{(chloroacetyl)(2-hydroxy-3-pyridinyl)amino}methyl]-N-cyclohexyl-3-methoxy-N-(1-methylethyl)benzamide

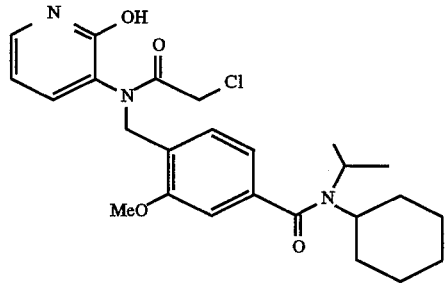

Chloroacetyl chloride (290 ml, 3.6 mmol) was added to a suspension of the compound of Example 15 (1.1 g, 2.77 mmol) in dry ether (150 ml) and tetrahydrofuran (50 ml) and the resulting mixture was stirred at room temperature for 18 hr. The reaction mixture, a homogeneous solution at this time, was quenched with water and aqueous sodium bicarbonate and extracted with ethyl acetate. The organic layer was washed with brine, dried (MgSO$_4$) and filtered. The filtrate was concentrated to give the title compound (1.32 g, 100%), m.p. 127°–129° C.

Anal. calcd. for $C_{25}H_{32}N_3O_4Cl \cdot 0.5\ H_2O$: C, 62.17; H, 6.89; N, 8.70; Cl, 7.34. Found: C, 62.26; H, 6.90; N, 8.34; Cl, 7.48.

EXAMPLE 17

Synthesis of N-cyclohexyl-4-[{2,3-dihydro-2-oxo-1H-pyrido(2,3-b)(1,4)oxazin-1-yl}methyl]-3-methoxy-N-(1-methylethyl)benzamide

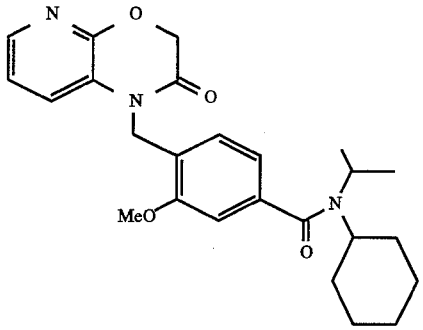

To a solution of the compound of Example 16 (300 mg, 0.63 mmol) in tetrahydrofuran (25 ml), sodium hydride (32 mg, 60% dispersion in mineral oil, 0.79 mmol) was added and the mixture was refluxed for 18 hr. After cooling to room temperature, the reaction was quenched by adding drops of cold water and 1N HCl. The mixture was treated with aqueous sodium bicarbonate to pH 10 and then extracted with ethyl acetate (2×150 ml). The organic layer was washed with brine, dried (MgSO$_4$), filtered and the filtrate concentrated in vacuo to give the crude product (280 mg). Chromatography on silica gel using ethyl acetate/acetone (98/2) as the eluent gave pure title compound (237 mg, 86%), m.p. (DSC) 189° C.

Anal calcd. for $C_{25}H_{31}N_3O_4 \cdot 0.4\ H_2O$: C, 67.52; H, 7.21; N, 9.45. Found: C, 67.59; H, 7.24; N, 9.05.

EXAMPLE 18

Synthesis of 3-methoxy-4-hydroxymethyl-N-isopropyl, N-cyclohexylbenzamide

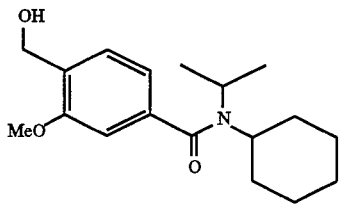

To a solution of 3-methoxy-4-bromomethyl-N-isopropyl, N-cyclohexylbenzamide (6.6 g, 18.13 mmol) in dimethylformamide (100 ml) was added sodium acetate (7.44 g, 90.66 mmol) and the mixture was heated with stirring at 80°–85° C. for 6 hr. The reaction mixture was cooled to room temperature and stirred for an additional 16 hr. A saturated solution of aqueous potassium carbonate (300 ml) was added and the reaction was stirred at room temperature for 48 hr. The reaction was concentrated under reduced pressure and neutralized with acetic acid. The aqueous layer was extracted with methylene chloride (2×400 ml) and washed with brine. After drying (MgSO$_4$), the organic fractions were concentrated and the crude product (6.56 g) chromatographed on silica gel using hexane/ethyl acetate (1/1) as the eluent to give pure title compound (4.5 g, 81%); m.p. (DSC) 135° C. $^1$H NMR (CDCl$_3$): 7.22 (d, J=8 Hz, 1H); 6.82 (m, 2H); 4.63 (d, J=7 Hz, 2H); 3.85 (s, 3H); 2.95 (m, 1H); 0.98–1.96 (complex band, 17H).

EXAMPLE 19

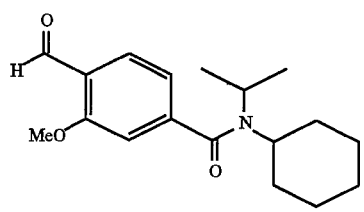

To a suspension of pyridinium chlorochromate (4.53 g, 21 mmol) in methylene chloride (50 ml) was added a solution of the compound of Example 18 (4.28 g, 14 mmol) in methylene chloride (50 ml). After stirring for 2.5 hr, the reaction was diluted with excess of dry ether (400 ml) and filtered through a pad of silica gel. The pad was washed with more ether (approx. 400 ml) and the combined filtrates were concentrated to give the title compound (4.2 g) as white solid, m.p. 133° C.

Anal. calcd. for $C_{18}H_{27}NO_3$: C, 71.26; H, 8.31; N, 4.62. Found: C, 71.00; H, 8.50; N, 4.50.

EXAMPLE 20

Human Platelet Receptor Binding Assay

Compounds of the invention were evaluated for their ability to inhibit specific binding of [$^3$H]PAF to human platelet membrane preparation. Human packed platelets were obtained from Lifesource, Inc. (Glenview, Ill.) and washed 3 times with 10 mM Trizma pH 7.0, 2 mM EDTA (dipotassium salt), 150 mM KCl and then once with 10 mM Trizma 7.4, 20 mM CaCl$_2$. The platelets were broken by freezing in a dry ice-ethanol bath, followed by thawing in 24° C. water baths. The preparation was centrifuged (40,000×g, 20 minutes, 4° C.) and the pellet suspended in 10 mM Trizma 7.4, 20 mM CaCl$_2$, 5 mg/ml human albumin. Protein concentration in the platelet membrane preparation was determined by the Lowry method [O. H. Lowry et al., J. Biol. Chem., 193, 265–275 (1951)]. Aliquots of the membrane preparation were stored at –70° C. Each preparation was characterized for PAF receptor number and dissociation constant (Kd). In binding assays 5 μl of test compound, solubilized in DMSO, was added to polypropylene tubes along with 0.75 nM [$^3$H]PAF and 200 mcl [0.075 nM] of membranes and 95 μl 10 mM Trizma 7.4, 20 mM CaCl$_2$, 5 mg/ml human albumin-Tubes were incubated for 30 minutes at 24° C. The incubation was terminated by adding 4 ml of ice-cold 10 mM Trizma pH 7.4, 20 mM CaCl$_2$ and 20 mg/ml BSA prior to vacuum filtration using Whatman GF/C filters. Filters were prepared and counted in a scintillation counter. All DPM values (disintergrations per minute) were corrected for background and isotope decay. Triplicate determinations for single doses were averaged. The amount of non-specific binding was subtracted from all dose averages, giving an amount of specific binding in all cases. The IC$_{50}$ values for the compounds of the invention were determined by the Allfit program using percent displacement data. (Allfit is a 'basic' computer program for simultaneous curve fitting of a family of signoidal dose-response curves using the four parameter logistic equation.)

Results are shown in Table I. In Table 1 "c-pent" means cyclopentyl; "c-hex" means cyclohexyl; "i-Pr" means isopropyl; "Me" means methyl; and "OMe" means methoxy.

TABLE I

| EX # | A—B | Y, Y' | X | R¹ | R² | PAF Inhibitor Activity Human Platelet Receptor Assay |
|---|---|---|---|---|---|---|
| 11 | —N=CH— | H, H | 3-Br | isoprop | c-hex | 2 nM |
| 10 | —N=CH— | H, H | 3-Me | c-pent | c-hex | 219 nM |
| 9 | —N=CH— | H, H | 2-OMe | c-pent | 3,5-dimethyl c-hex | 163 nM |
| 17 | —CH=N— | =O | 3-OMe | isoprop | c-hex | 505 nM |

What is claimed is:

1. A compound of the formula

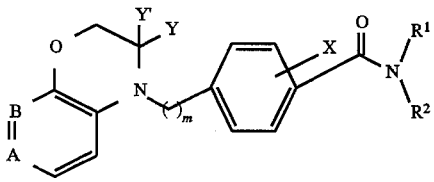

or a pharmaceutically acceptable salt thereof wherein

A-B is selected from the group of —N=CH— and —CH=N—;

m is an integer of from 1 to 4;

R₁ and R₂ are independently selected from the group consisting of straight or branched alkyl of about 1 to 6 carbon atoms and cycloalkyl of 3 to 7 ring carbon atoms, the ring carbon atoms optionally substituted with one or more alkyl groups having 1 to 6 carbon atoms each;

X is selected from the group consisting of hydrogen, alkyl of 1 to 6 carbon atoms, alkoxy of 1 to 6 carbon atoms and halogen; and Y and Y' are both hydrogen or taken together are =O.

2. A compound according to claim 1 of the formula wherein A-B is —N=CH— and m is 1.

3. A compound according to claim 2 wherein at least one of R¹ and R² is cycloalkyl, optionally substituted with one or more alkyl groups.

4. A compound according to claim 3 wherein Y and Y' are hydrogen.

5. A compound according to claim 4 which is cis-N-cyclopentyl-4-[(2,3-dihydro-1H-pyrido[3,4-b][1,4]-oxazin-1-yl)methyl-N-(3,5-dimethylcyclohexyl)-2-methoxybenzamide.

6. A compound according to claim 4 which is N-cyclohexyl-N-cyclopentyl-4-[(2,3-dihydro-1H-pyrido[3,4-b][1,4]oxazin-1-yl)methyl]-3-methyl-benzamide.

7. A compound according to claim 4 which is 3-bromo-N-cyclohexyl-4-[(2,3-dihydro-1H-pyrido[3,4-b][1,4]oxazin-1-yl)methyl]-N-(1-methylethyl)-benzamide.

8. A compound according to claim 1 of the formula wherein A-B is —CH=N— and m is 1.

9. A compound according to claim 8 wherein at least one of R¹ and R² is cycloalkyl, optionally substituted with one or more alkyl groups.

10. A compound according to claim 9 wherein Y and Y' taken together are =O.

11. A compound according to claim 9 wherein Y and Y' are hydrogen.

12. A compound according to claim 10 which is N-cyclohexyl-4-[{2,3-dihydro-2-oxo-1H-pyrido(2,3-b)(1,4)oxazin-1-yl}methyl]-3-methoxy-N-(1-methylethyl)benzamide.

13. A pharmaceutical composition comprising a therapeutically effective amount of a compound of the formula

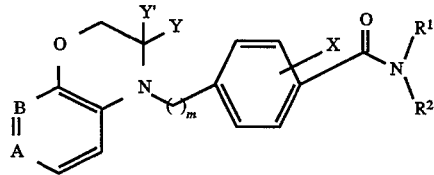

or a pharmaceutically acceptable salt thereof wherein

Y and Y' are both hydrogen or taken together are =O;

R₁ and R₂ are independently selected from the group consisting of straight or branched alkyl of about 1 to 6 carbon atoms and cycloalkyl of 3 to 7 ring carbon atoms, the ring carbon atoms optionally substituted with one or more alkyl groups having 1 to 6 carbon atoms each; and X is selected from the group consisting of hydrogen, alkyl of 1 to 6 carbon atoms, alkoxy of 1 to 6 carbon atoms and halogen; and a pharmaceutically acceptable carrier.

14. A pharmaceutical composition according to claim 13 wherein A-B is —N=CH— and m is 1.

15. A pharmaceutical composition according to claim 14 wherein at least one of R¹ and R² is cycloalkyl, optionally substituted with one or more alkyl groups.

16. A pharmaceutical composition according to claim 15 wherein Y and Y' are hydrogen.

17. A pharmaceutical composition according to claim 16 wherein the compound is cis-N-cyclopentyl-4-[(2,3- dihydro-1H-pyrido[3,4-b][1,4]-oxazin-1-yl) methyl-N-(3,5-dimethylcyclohexyl)-2-methoxybenzamide.

18. A pharmaceutical composition according to claim 16 wherein the compound is N-cyclohexyl-N-cyclopentyl-4-[(2,3-dihydro-1H-pyrido[3,4-b][1,4]oxazin-1-yl)methyl]-3-methyl-benzamide.

19. A pharmaceutical composition according to claim 16 wherein the compound is 3-bromo-N-cyclohexyl-4-[(2,3-dihydro-1H-pyrido[3,4-b][1,4]oxazin-1-yl)methyl]-N-(1-methylethyl)-benzamide.

20. A pharmaceutical composition according to claim 13 wherein A-B is —CH=N— and m is 1.

21. A pharmaceutical composition according to claim 20 wherein at least one of $R^1$ and $R^2$ is cycloalkyl, optionally substituted with one or more alkyl groups.

22. A pharmaceutical composition according to claim 21 wherein Y and Y' taken together are =O.

23. A pharmaceutical composition according to claim 21 wherein Y and Y' are hydrogen.

24. A pharmaceutical composition according to claim 22 wherein the compound is N-cyclohexyl-4-[{2,3-dihydro-2-oxo-1H-pyrido(2,3-b)(1,4)oxazin-1-yl}methyl]-3-methoxy-N-(1-methylethyl)benzamide.

25. A method for treating a disease mediated by platelet activating factor comprising administering to a patient in need of such treatment a therapeutically effective amount of a compound of the formula

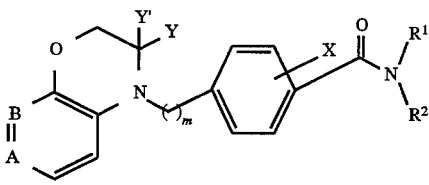

or a pharmaceutically acceptable salt thereof wherein
Y and Y' are both hydrogen or taken together are =O;
$R_1$ and $R_2$ are independently selected from the group consisting of straight or branched alkyl of about 1 to 6 carbon atoms and cycloalkyl of 3 to 7 ring carbon atoms, the ring carbon atoms optionally substituted with one or more alkyl groups having 1 to 6 carbon atoms each; and X is selected from the group consisting of hydrogen, alkyl of 1 to 6 carbon atoms, alkoxy of 1to 6 carbon atoms and halogen.

26. A method according to claim 25 wherein A-B is —N=CH— and m is 1.

27. A method according to claim 26 wherein at least one of $R^1$ and $R^2$ is cycloalkyl, optionally substituted with one or more alkyl groups.

28. A method according to claim 27 wherein Y and Y' are hydrogen.

29. A method according to claim 25 of the formula wherein A-B is —CH=N— and m is 1.

30. A method according to claim 29 wherein at least one of $R^1$ and $R^2$ is cycloalkyl, optionally substituted with one or more alkyl groups.

31. A method according to claim 30 wherein Y and Y' taken together are =O.

32. A method according to claim 30 wherein Y and Y' are hydrogen.

33. A method according to claim 25 wherein the compound is selected from the group consisting of:

cis-N-cyclopentyl-4-[(2,3-dihydro-1H-pyrido[3,4-b][1,4]-oxazin-1-yl)methyl-N-(3,5-dimethylcyclohexyl)-2-methoxybenzamide;

N-cyclohexyl-N-cyclopentyl-4-[(2,3-dihydro-1H-pyrido[3,4-b][1,4]oxazin-1-yl)methyl]-3-methyl-benzamide;

3-bromo-N-cyclohexyl-4-[(2,3-dihydro-1H-pyrido[3,4-b][1,4]oxazin-1-yl)methyl]-N-(1-methylethyl)-benzamide; and N-cyclohexyl-4-[{2,3-dihydro-2-oxo-1H-pyrido(2,3-b)(1,4)oxaz in-1-yl}methyl]-3-methoxy-N-(1-methylethyl)benzamide.

34. A method according to claim 26 wherein the disease is asthma.

35. A method according to claim 26 wherein the disease is septic shock.

* * * * *

UNITED STATES PATENT AND TRADEMARK OFFICE
CERTIFICATE OF CORRECTION

PATENT NO. : 5,652,363

DATED : July 29, 1997

INVENTOR(S): ISH K. KHANNA ET AL.

Page 1 of 2

It is certified that error appears in the above-identified patent and that said Letters Patent is hereby corrected as shown below:

On the title page, item

[73 Assignee]

"C.D. Searle & Co., Skokie, Ill." should read
--G.D. Searle & Co., Skokie, Ill.--.

COLUMN 5

Line 28, "-COO$_7$" should read ---COOR$_7$--.

COLUMN 11

Scheme V, "Sio" should read --SiO--.

COLUMN 15

Line 41, "temperatures" should read --temperature--.

COLUMN 23

Line 48, "oxazin-$_1$-yl)" should read --oxazin-1-yl)--.

UNITED STATES PATENT AND TRADEMARK OFFICE
CERTIFICATE OF CORRECTION

PATENT NO. : 5,652,363

DATED : July 29, 1997

INVENTOR(S): ISH K. KHANNA ET AL.

It is certified that error appears in the above-identified patent and that said Letters Patent is hereby corrected as shown below:

COLUMN 24

Line 17, "Structural" should read --structural--.

COLUMN 28

Line 53, "albumin-Tubes" should read --albumin. Tubes--.

COLUMN 32

Line 4, "1to 6" should read --1 to 6--; and
    Line 34, "oxaz in" should read --oxazin--.

Signed and Sealed this

Twenty-eighth Day of April, 1998

*Attest:*

BRUCE LEHMAN

*Attesting Officer*    *Commissioner of Patents and Trademarks*